United States Patent
Ju et al.

(10) Patent No.: US 11,504,188 B2
(45) Date of Patent: Nov. 22, 2022

(54) MRI-GUIDED STEREOTACTIC SURGERY METHOD AND MRI-COMPATIBLE STEREOTACTIC SURGERY DEVICE

(71) Applicant: NATIONAL CHENG KUNG UNIVERSITY, Tainan (TW)

(72) Inventors: Ming-Shaung Ju, Tainan (TW); Chou-Ching Lin, Tainan (TW); Bing-Lin Ho, Pingtung County (TW); Huang-Lin Chen, Kaohsiung (TW); Yu-Nung Peng, Hsinchu County (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 300 days.

(21) Appl. No.: 16/691,626

(22) Filed: Nov. 22, 2019

(65) Prior Publication Data

US 2021/0153950 A1    May 27, 2021

(51) Int. Cl.
| | |
|---|---|
| *A61B 34/20* | (2016.01) |
| *A61B 90/11* | (2016.01) |
| *G01R 33/28* | (2006.01) |
| *A61B 34/10* | (2016.01) |
| *A61B 17/00* | (2006.01) |
| *A61B 90/00* | (2016.01) |

(52) U.S. Cl.
CPC ............. *A61B 34/20* (2016.02); *A61B 90/11* (2016.02); *G01R 33/285* (2013.01); *A61B 2017/00402* (2013.01); *A61B 2034/107* (2016.02); *A61B 2034/2051* (2016.02); *A61B 2090/374* (2016.02); *A61B 2562/182* (2013.01)

(58) Field of Classification Search
CPC ..................... A61B 34/20; A61B 90/11; A61B 2017/00402; A61B 2034/107; A61B 2034/2051; A61B 2090/374; A61B 2562/182; A61B 2034/2059; A61B 2034/2065; A61B 90/10; G01R 33/285
See application file for complete search history.

(56) References Cited

U.S. PATENT DOCUMENTS

| | | | |
|---|---|---|---|
| 2011/0077504 A1* | 3/2011 | Fischer | A61B 34/30 606/130 |
| 2016/0100900 A1* | 4/2016 | Madhani | A61B 34/71 901/10 |
| 2018/0049826 A1* | 2/2018 | Fischer | A61B 34/30 |

\* cited by examiner

*Primary Examiner* — Joel Lamprecht
(74) *Attorney, Agent, or Firm* — CKC & Partners Co., LLC

(57) ABSTRACT

A MRI-guided stereotactic surgery method including the following steps: assigning coordinates of a surgery target point of a surgery cannula and an insertion direction of the surgery cannula; performing coordinate transformation to transform the coordinates of the surgery target point into an insertion position of the surgery target point; substituting the insertion position and the insertion direction into an inverse kinematics model to obtain five parameters respectively corresponding to five degrees of freedom of a MRI-compatible stereotactic surgery device; controlling the MRI-compatible stereotactic surgery device according to the parameters to start a stereotactic surgery procedure, thereby inserting the surgery cannula; obtaining an actual cannula position according to a magnetic resonance (MR) image; comparing the actual cannula position with the surgery target point to obtain an actual position vector; and withdrawing the surgery cannula to finish the stereotactic surgery procedure when the actual position vector is acceptable.

15 Claims, 7 Drawing Sheets

MRI-GUIDED STEREOTACTIC SURGERY METHOD AND MRI-COMPATIBLE STEREOTACTIC SURGERY DEVICE

BACKGROUND

Field of Invention

The present invention relates to a MRI-guided stereotactic surgery method and a MRI-compatible stereotactic surgery device.

Description of Related Art

Stereotactic surgery is an important core technology that has been widely used in the field of brain neurosurgery for biopsy, ablation and deep brain stimulation (DBS). The stereotactic surgery is operated through a small keyhole, and thus it is hard to confirm the position of distal end of a cannula of surgical devices, and human errors and brain shift may occur. The performance of the traditional stereotactic surgery merely depends on accuracies of surgical devices positioning and pre-operation images. Introducing intraoperative magnetic resonance images (MRI) could provide real-time magnetic resonance (MR) image, thereby enhancing the accuracy of the stereotactic surgery.

In addition, integrating intraoperative magnetic resonance images (MRI) and surgical robots can further enhance the accuracy and the efficiency of the stereotactic surgery and enhance safety of the patients. However, if the surgical robots would like to be operated in MRI scanner room, the surgical robots need to be designed to be MRI-compatible. Furthermore, the volume of the MRI-compatible robots is also limited due to limitation of the MRI operating space.

SUMMARY

An object of the present invention is to provide a MRI-guided stereotactic surgery method and a MRI-compatible stereotactic surgery device, thereby enhancing the accuracy and the efficiency of the stereotactic surgery and enhancing safety of the patients.

To achieve the above object, the present invention provides a MRI-guided stereotactic surgery method including the following steps: assigning coordinates of a surgery target point of a surgery cannula and an insertion direction of the surgery cannula; performing coordinate transformation to transform the coordinates of the surgery target point into an insertion position of the surgery target point; substituting the insertion position and the insertion direction into an inverse kinematics model to obtain five parameters respectively corresponding to five degrees of freedom of a MRI-compatible stereotactic surgery device; controlling the MRI-compatible stereotactic surgery device according to the parameters to start a stereotactic surgery procedure, thereby inserting the surgery cannula; obtaining an actual cannula position according to a magnetic resonance (MR) image providing by a magnetic resonance imaging (MRI) scanner; comparing the actual cannula position with the surgery target point to obtain an actual position vector; and withdrawing the surgery cannula to finish the stereotactic surgery procedure when the actual position vector is acceptable.

In accordance with one or more embodiments of the invention, when the actual position vector is not acceptable, the MRI-guided stereotactic surgery method further includes: calculating a compensation quantity according to the actual position vector; adjusting three of the parameters according to the compensation quantity; controlling the MRI-compatible stereotactic surgery device according to the adjusted parameters, thereby withdrawing the surgery cannula, adjusting the insertion position and the insertion direction of the surgery cannula, and inserting the surgery cannula again; updating the actual cannula position according to the MR image updating by the MRI scanner; comparing the updated actual cannula position with the surgery target point to update the actual position vector; and withdrawing the surgery cannula to finish the stereotactic surgery procedure when the updated actual position vector is acceptable.

In accordance with one or more embodiments of the invention, the compensation quantity is calculated by a Taylor series expansion and by utilizing a Jacobian square matrix based on the actual position vector.

In accordance with one or more embodiments of the invention, the parameters are obtained by utilizing a Newton-Raphson iterative method.

To achieve the above object, the present invention further provides a MRI-compatible stereotactic surgery device including a remote center of motion (RCM) stage and a guiding element. The RCM stage includes a base plate, a horizontal arc-shaped slide, a horizontal sliding stage disposed on the horizontal arc-shaped slide, a vertical arc-shaped slide, and a vertical sliding stage disposed on the vertical arc-shaped slide. Two ends of the horizontal arc-shaped slide are fixed on the base plate. The horizontal sliding stage includes a first friction wheel in rolling friction contact with the horizontal arc-shaped slide. The horizontal sliding stage moves along the horizontal arc-shaped slide in a first direction through the first friction wheel. The horizontal arc-shaped slide includes a first driven wheel for recording relative movement between the first friction wheel and the horizontal arc-shaped slide. One end of the vertical arc-shaped slide is fixed on the horizontal sliding stage. The vertical sliding stage includes a second friction wheel in rolling friction contact with the vertical arc-shaped slide. The vertical sliding stage moves along the vertical arc-shaped slide in a second direction through the second friction wheel. The vertical arc-shaped slide includes a second driven wheel for recording relative movement between the second friction wheel and the vertical arc-shaped slide. The guiding element is fixed on the vertical sliding stage of the RCM stage. The guiding element includes a surgery cannula. The guiding element is configured to guide the surgery cannula to move along a third direction, a fourth direction, and a fifth direction.

In accordance with one or more embodiments of the invention, the horizontal arc-shaped slide is ½ circular arc-shaped, and the vertical arc-shaped slide is ¼ circular arc-shaped.

In accordance with one or more embodiments of the invention, the MRI-compatible stereotactic surgery device further includes at least one electromagnetic interference shielding cover configured to cover the horizontal sliding stage, the vertical sliding stage, and the guiding element. The MRI-compatible stereotactic surgery device further includes plural fixed accessories configured to fix the base plate, the horizontal arc-shaped slide, the horizontal sliding stage, the vertical arc-shaped slide, the vertical sliding stage, the guiding element, the first friction wheel, the first driven wheel, the second friction wheel, and the second driven wheel. The fixed accessories are made of non-ferromagnetic material. The base plate, the horizontal arc-shaped slide, the horizontal sliding stage, the vertical arc-shaped slide, the vertical sliding stage, and the guiding element are made of engineering plastics. The first friction wheel, the first driven wheel, the second friction wheel, and the second driven wheel are made of synthetic rubber.

In accordance with one or more embodiments of the invention, the guiding element further includes two self-aligning universal ceramic bearings mounted on the surgery cannula so as to adjust an insertion direction of the surgery cannula.

In accordance with one or more embodiments of the invention, the horizontal sliding stage further includes a first piezoelectric motor and the vertical sliding stage further includes a second piezoelectric motor. The first piezoelectric motor is configured to drive the first friction wheel, such that the horizontal sliding stage moves along the horizontal arc-shaped slide in the first direction. The second piezoelectric motor is configured to drive the second friction wheel, such that the vertical sliding stage to move along the vertical arc-shaped slide in the second direction.

In accordance with one or more embodiments of the invention, the horizontal sliding stage further includes a first optical encoder connected to the first driven wheel and the vertical sliding stage further includes a second optical encoder connected to the second driven wheel. The first optical encoder is configured to record relative movement between the first friction wheel and the horizontal arc-shaped slide. The second optical encoder is configured to record relative movement between the second friction wheel and the vertical arc-shaped slide.

In accordance with one or more embodiments of the invention, the guiding element further includes a rotary piezoelectric motor and two linear piezoelectric motors. The rotary piezoelectric motor is configured to drive the surgery cannula to move along the third direction. Two linear piezoelectric motors are respectively configured to drive the surgery cannula to move along the fourth direction and the fifth direction. The rotary piezoelectric motor drives the surgery cannula through a synchronous timing belt and a belt pulley.

In accordance with one or more embodiments of the invention, the guiding element further includes a rotary piezoelectric motor and a linear piezoelectric motor. The rotary piezoelectric motor is configured to drive the surgery cannula to move along the third direction. The linear piezoelectric motor is configured to drive the surgery cannula to move along the fourth direction. The rotary piezoelectric motor drives the surgery cannula through a synchronous timing belt and a belt pulley. The fifth direction is reserved for manual insertion of the surgery cannula by a surgeon.

In accordance with one or more embodiments of the invention, the MRI-compatible stereotactic surgery device further includes a controlling computer connected to the first piezoelectric motor, the second piezoelectric motor, the linear piezoelectric motors, and the rotary piezoelectric motor. The controlling computer is configured to drive the first piezoelectric motor, the second piezoelectric motor, the linear piezoelectric motors, and the rotary piezoelectric motor, thereby controlling the MRI-compatible stereotactic surgery device with five degrees of freedom.

In accordance with one or more embodiments of the invention, the controlling computer is further configured to reduce relative slide error between the first friction wheel and the horizontal arc-shaped slide according to relative movement between the first friction wheel and the horizontal arc-shaped slide which is recorded by the first optical encoder. The controlling computer is further configured to reduce relative slide error between the second friction wheel and the vertical arc-shaped slide according to relative movement between the second friction wheel and the vertical arc-shaped slide which is recorded by the second optical encoder.

In accordance with one or more embodiments of the invention, the MRI-compatible stereotactic surgery device further includes plural signal lines connected from the controlling computer to the first piezoelectric motor, the second piezoelectric motor, the linear piezoelectric motors, and the rotary piezoelectric motor. The signal lines are covered by electromagnetic interference material.

In accordance with one or more embodiments of the invention, the controlling computer is built in a forward kinematics model and an inverse kinematics model.

In accordance with one or more embodiments of the invention, the controlling computer is further configured to: assign coordinates of a surgery target point of the surgery cannula and an insertion direction of the surgery cannula; perform coordinate transformation to transform the coordinates of the surgery target point into an insertion position of the surgery target point; assign a surgery target point corresponding to an insertion position and an insertion direction of the surgery cannula; control the MRI-compatible stereotactic surgery device according to the parameters to start a stereotactic surgery procedure, thereby inserting the surgery cannula; obtain an actual cannula position according to a MR image providing by a MRI scanner; compare the actual cannula position with the surgery target point to obtain an actual position vector; and control the linear piezoelectric motors to withdraw the surgery cannula to finish the stereotactic surgery procedure when the actual position vector is acceptable.

In accordance with one or more embodiments of the invention, when the actual position vector is not acceptable, the controlling computer is further configured to: calculate a compensation quantity according to the actual position vector; drive the linear piezoelectric motors and the rotary piezoelectric motor according to the compensation quantity, thereby withdrawing the surgery cannula, adjusting the insertion position and the insertion direction of the surgery cannula, and inserting the surgery cannula again; update the actual cannula position according to the MR image updating by the MRI scanner; compare the updated actual cannula position with the surgery target point to update the actual position vector; and withdraw the surgery cannula to finish the stereotactic surgery procedure when the updated actual position vector is acceptable.

In accordance with one or more embodiments of the invention, the compensation quantity is calculated by a Taylor series expansion and by utilizing a Jacobian square matrix based on the actual position vector.

In accordance with one or more embodiments of the invention, the parameters are obtained by utilizing a Newton-Raphson iterative method.

BRIEF DESCRIPTION OF THE DRAWINGS

The invention can be more fully understood by reading the following detailed description of the embodiment, with reference made to the accompanying drawings as follows.

DETAILED DESCRIPTION

Specific embodiments of the present invention are further described in detail below with reference to the accompanying drawings, however, the embodiments described are not intended to limit the present invention and it is not intended for the description of operation to limit the order of implementation. Moreover, any device with equivalent functions that is produced from a structure formed by a recombination of elements shall fall within the scope of the present invention. Additionally, the drawings are only illustrative and are not drawn to actual size.

Moreover, unless specified otherwise, "first," "second," or the like are not intended to imply a temporal aspect, a spatial aspect, an ordering, etc. Rather, such terms are merely used as identifiers, names, etc. for features, elements, items, etc. For example, a first element and a second element generally correspond to element A and element B or two different or two identical elements or the same element.

Figure 1:
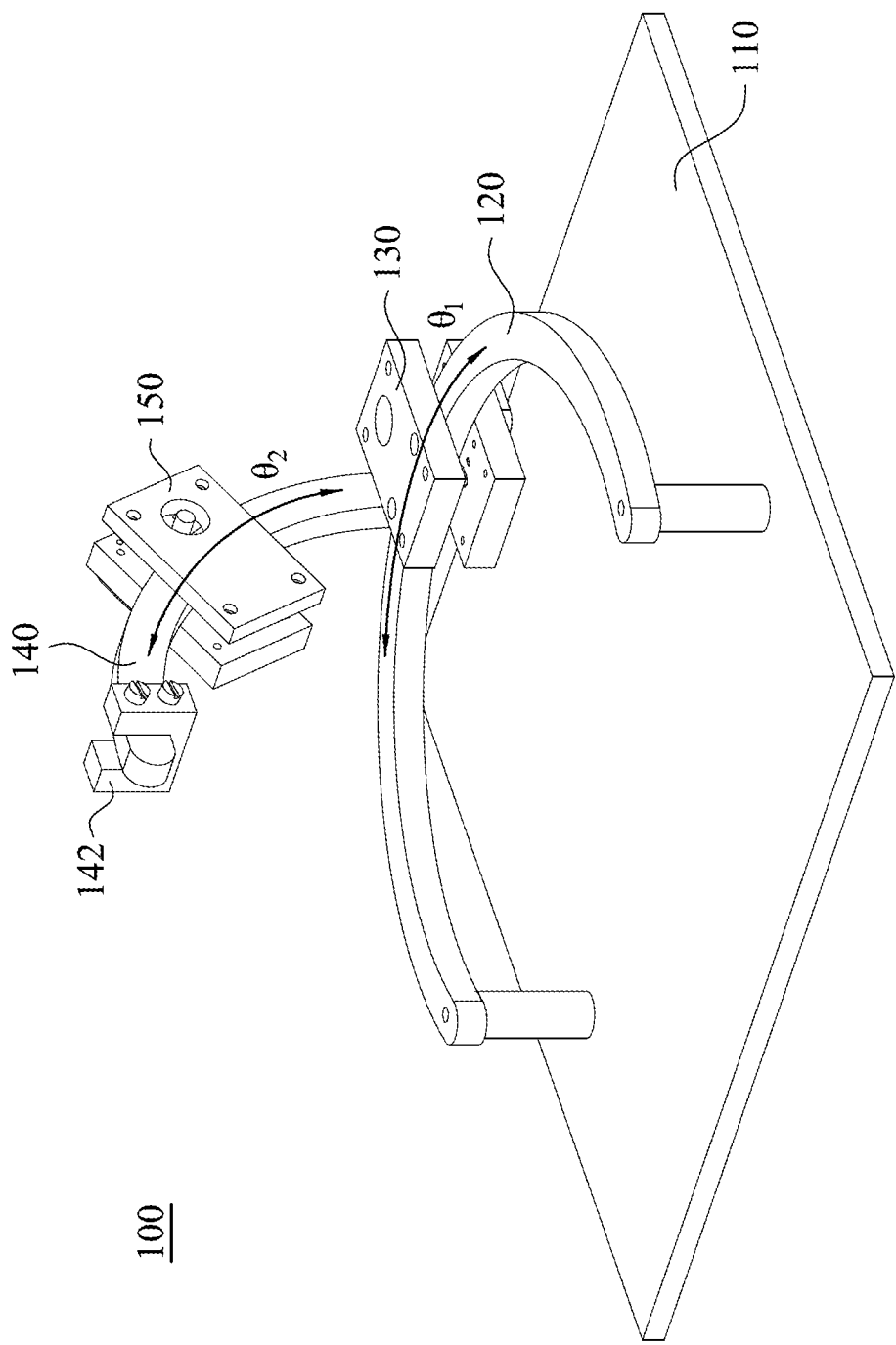
FIG. 1 illustrates a remote center of motion (RCM) stage of a MRI-compatible stereotactic surgery device according to some embodiments of the present invention.

FIG. 1 illustrates a remote center of motion (RCM) stage 100 of a MRI-compatible stereotactic surgery device according to some embodiments of the present invention. The RCM stage 100 includes a base plate 110, a horizontal arc-shaped slide 120, a horizontal sliding stage 130, a vertical arc-shaped slide 140, and a vertical sliding stage 150.

Figure 2:
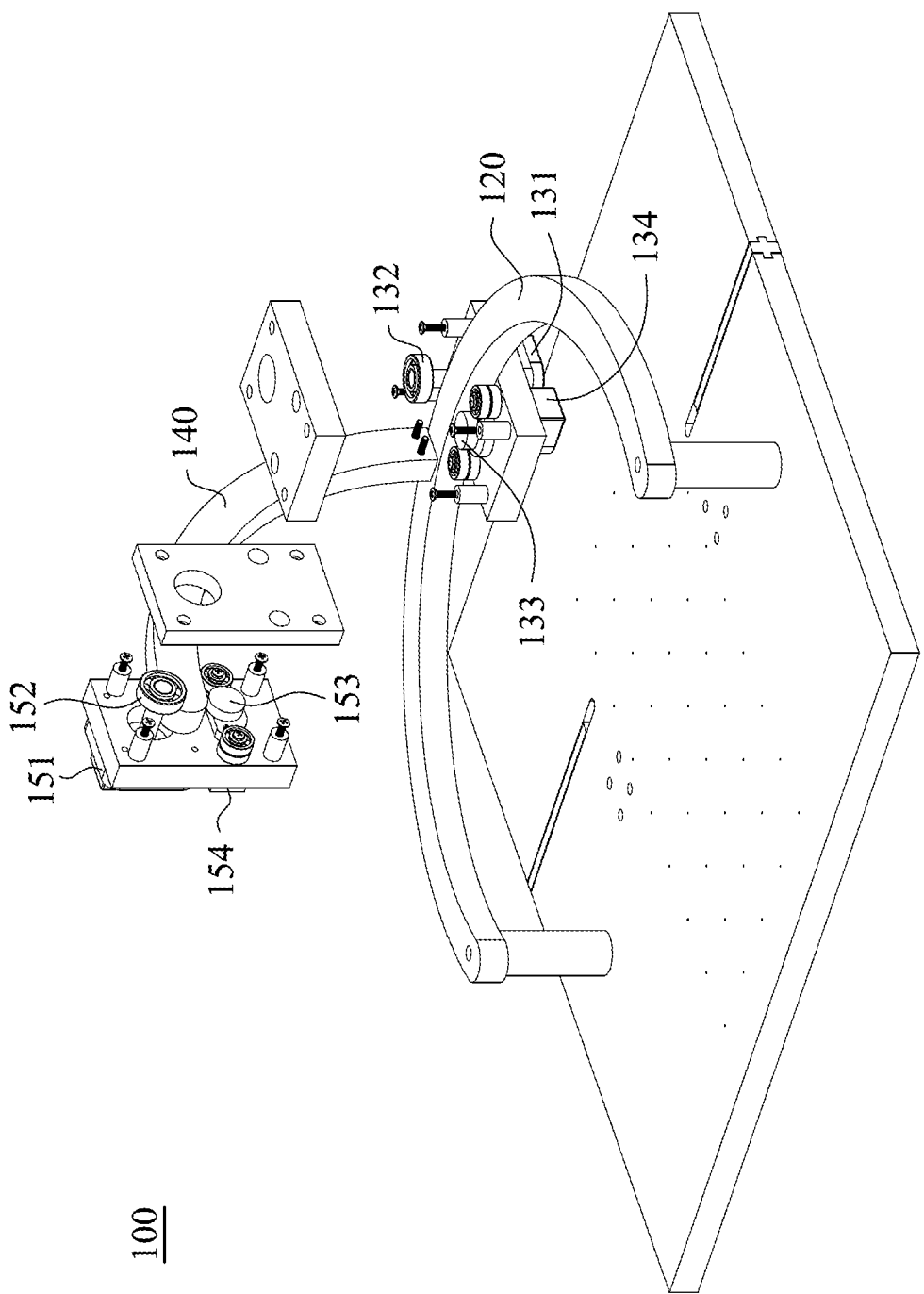
FIG. 2 illustrates an explosion drawing of a horizontal sliding stage and a vertical sliding stage of the RCM stage of the MRI-compatible stereotactic surgery device according to some embodiments of the present invention.

As shown in FIG. 1, the horizontal arc-shaped slide 120 is ½ circular arc-shaped, and two ends of the horizontal arc-shaped slide 120 are fixed on the base plate 110. The horizontal sliding stage 130 is disposed on the horizontal arc-shaped slide 120. FIG. 2 illustrates an explosion drawing of the horizontal sliding stage 130 and the vertical sliding stage 150 of the RCM stage 100 of the MRI-compatible stereotactic surgery device according to some embodiments of the present invention. The horizontal sliding stage 130 includes a piezoelectric motor 131, a friction wheel 132, a driven wheel 133, and an optical encoder 134 electrically connected to the driven wheel 133. The friction wheel 132 is placed onto shaft of the piezoelectric motor 131, and the friction wheel 132 is disposed to be in rolling friction contact with the horizontal arc-shaped slide 120. The piezoelectric motor 131 is configured to drive the friction wheel 132. Specifically, the friction wheel 132 is caused to rotate by means of the piezoelectric motor 131. When the friction wheel 132 rotates, there is friction force generating between the friction wheel 132 and the horizontal arc-shaped slide 120, so as to drive the horizontal sliding stage 130 to move along the horizontal arc-shaped slide 120 in a first direction $\theta_1$. The relative movement between the friction wheel 132 and the horizontal arc-shaped slide 120 may cause the relative slide error between the friction wheel 132 and the horizontal arc-shaped slide 120, and therefore the driven wheel 133 and the optical encoder 134 are configured to record the relative movement between the friction wheel 132 and the horizontal arc-shaped slide 120. Specifically, the amount of rotation of the driven wheel 133 corresponds to the relative movement between the friction wheel 132 and the horizontal arc-shaped slide 120, and the optical encoder 134 can measure the amount of rotation of the driven wheel 133, and thus the relative movement between the friction wheel 132 and the horizontal arc-shaped slide 120 can be recorded. Once the relative movement between the friction wheel 132 and the horizontal arc-shaped slide 120 is considered, the relative slide error between the friction wheel 132 and the horizontal arc-shaped slide 120 could be reduced by means of some known methods.

As shown in FIG. 1, the vertical arc-shaped slide 140 is ¼ circular arc-shaped, and one end of the vertical arc-shaped slide 140 is fixed on the horizontal sliding stage 130. The vertical arc-shaped slide 140 and the horizontal arc-shaped slide 120 are not in contact with each other. Specifically, when the horizontal sliding stage 130 moves along the horizontal arc-shaped slide 120 in the first direction $\theta_1$, the vertical arc-shaped slide 140 fixed on the horizontal sliding stage 130 also moves in the first direction $\theta_1$ accordingly.

As shown in FIG. 1 and FIG. 2, the vertical sliding stage 150 is disposed on the vertical arc-shaped slide 140. The vertical sliding stage 150 includes a piezoelectric motor 151, a friction wheel 152, a driven wheel 153, and an optical encoder 154 electrically connected to the driven wheel 153. The friction wheel 152 is placed onto shaft of the piezoelectric motor 151, and the friction wheel 152 is disposed to be in rolling friction contact with the vertical arc-shaped slide 140. The piezoelectric motor 151 is configured to drive the friction wheel 152. Specifically, the friction wheel 152 is caused to rotate by means of the piezoelectric motor 151. When the friction wheel 152 rotates, there is friction force generating between the friction wheel 152 and the vertical arc-shaped slide 140, so as to drive the vertical sliding stage 150 to move along the vertical arc-shaped slide 140 in a second direction $\theta_2$. It is worth mentioning that, as shown in FIG. 1, the vertical arc-shaped slide 140 further includes a stop piece 142, so as to prevent the vertical sliding stage 150 sliding out of the vertical arc-shaped slide 140. The relative movement between the friction wheel 152 and the vertical arc-shaped slide 140 may cause the relative slide error between the friction wheel 152 and the vertical arc-shaped slide 140, and therefore the driven wheel 153 and the optical encoder 154 are configured to record the relative movement between the friction wheel 152 and the vertical arc-shaped slide 140. Specifically, the amount of rotation of the driven wheel 153 corresponds to the relative movement between the friction wheel 152 and the vertical arc-shaped slide 140, and the optical encoder 154 can measure the amount of rotation of the driven wheel 153, and thus the relative movement between the friction wheel 152 and the vertical arc-shaped slide 140 can be recorded. Once the relative movement between the friction wheel 152 and the vertical arc-shaped slide 140 is considered, the relative slide error between the friction wheel 152 and the vertical arc-shaped slide 140 could be reduced by means of some known methods.

It is worth mentioning that the movement of the horizontal sliding stage 130 and the movement of the vertical sliding stage 150 are driven by rolling friction force. Comparing with the known gear driving devices, the present disclosure could avoid the problem of position errors caused by gear backlash.

It is worth mentioning that, when the horizontal sliding stage 130 moves along the horizontal arc-shaped slide 120, the movement drag of the horizontal sliding stage 130 is only friction between the horizontal sliding stage 130 and the horizontal arc-shaped slide 120, and when the vertical sliding stage 150 moves along the vertical arc-shaped slide 140, the movement drag of the vertical sliding stage 150 is only the friction between the vertical sliding stage 150 and the vertical arc-shaped slide 140 and the weight of the vertical sliding stage 150. Therefore, such a low drag design can reduce the high torque requirement of the driving motor (i.e., the piezoelectric motor 131 and the piezoelectric motor 151), and therefore the volume of the piezoelectric motor 131 and the piezoelectric motor 151 could be reduced. In other words, the volume of the MRI-compatible stereotactic surgery device 10 could be reduced accordingly.

Figure 3:
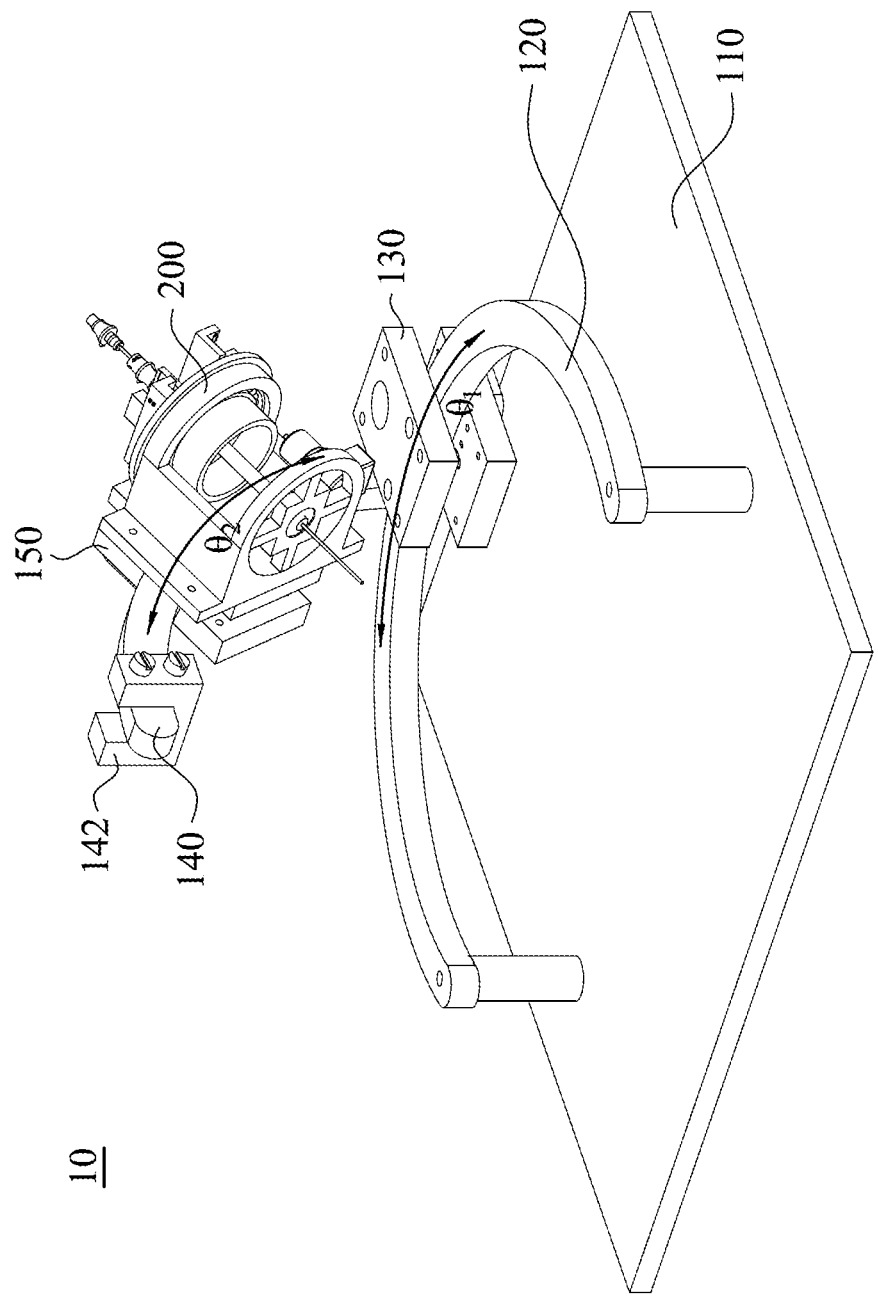
FIG. 3 illustrates the MRI-compatible stereotactic surgery device according to some embodiments of the present invention.

FIG. 3 illustrates the MRI-compatible stereotactic surgery device 10 according to some embodiments of the present invention. As shown in FIG. 1 and FIG. 3, the MRI-compatible stereotactic surgery device 10 includes the RCM stage 100 and a guiding element 200. The guiding element 200 is fixed on the vertical sliding stage 150 of the RCM stage 100. Specifically, when the horizontal sliding stage 130 moves along the horizontal arc-shaped slide 120 in the first direction $\theta_1$ and/or the vertical sliding stage 150 moves along the vertical arc-shaped slide 140 in the second direction $\theta_2$, the guiding element 200 fixed on the vertical sliding stage 150 also moves in the first direction $\theta_1$ and/or the second direction $\theta_2$ accordingly.

Figure 4:
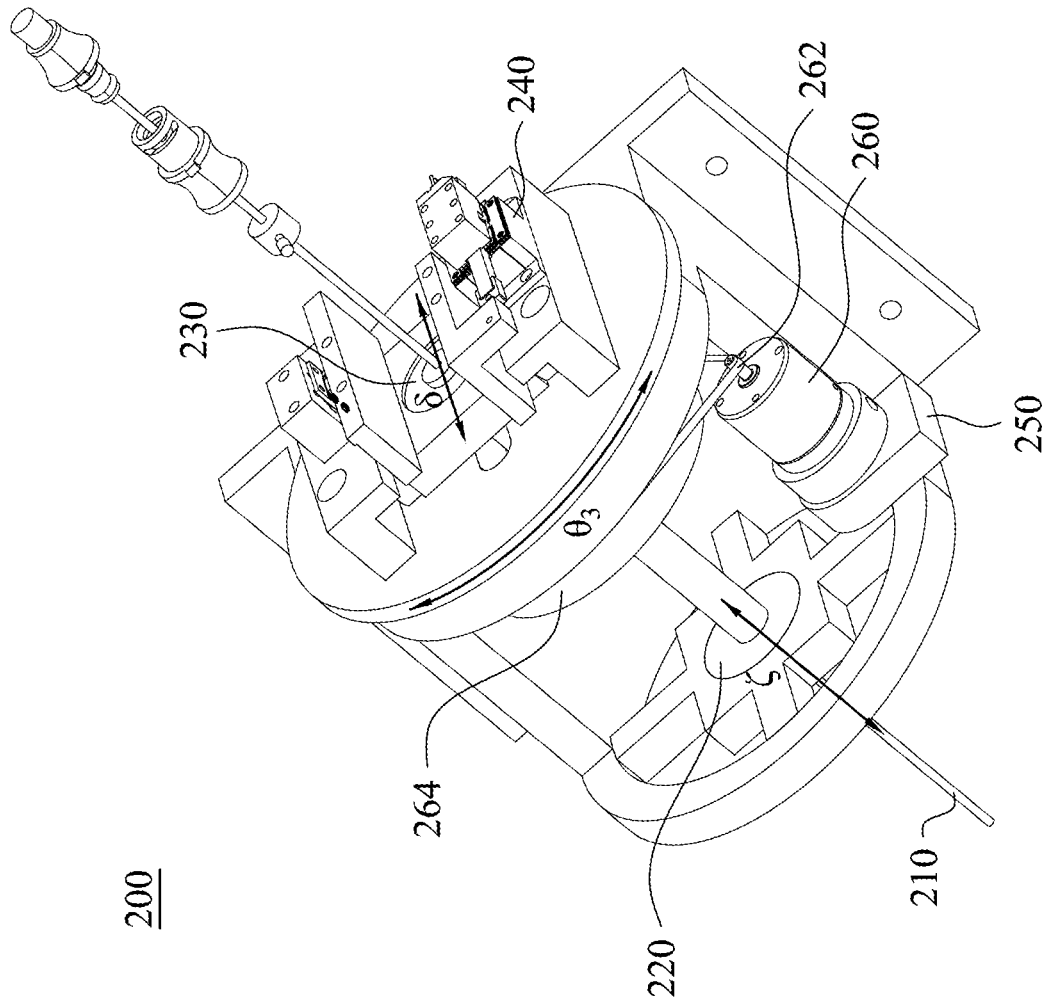
FIG. 4 illustrates a guiding element of the MRI-compatible stereotactic surgery device according to some embodiments of the present invention.

FIG. 4 illustrates the guiding element 200 of the MRI-compatible stereotactic surgery device 10 according to some embodiments of the present invention. As shown in FIG. 3 and FIG. 4, the guiding element 200 includes a surgery cannula 210, two self-aligning universal ceramic bearings 220 and 230, a rotary piezoelectric motor 260, and two linear piezoelectric motors 240 and 250. Two self-aligning universal ceramic bearings 220 and 230 are fixed on the frame of guiding element 200. The surgery cannula 210 is mounted on two sides of the self-aligning universal ceramic bearings 220 and 230, thereby allowing adjusting an insertion direction (i.e., a tilt angle) of the surgery cannula 210 within a limited range.

The rotary piezoelectric motor 260 and the linear piezoelectric motors 240 are respectively configured to drive the surgery cannula 210 to move along the third direction $\theta_3$ and the fourth direction $\delta$. The rotary piezoelectric motor 260 drives the surgery cannula 210 through a synchronous timing belt 262 and a belt pulley 264. The linear piezoelectric motor 250 is configured to drive the surgery cannula 210 to move along the fifth direction $\zeta$. Specifically, the insertion direction (i.e., a tilt angle) of the surgery cannula 210 corresponds to the third direction $\theta_3$ and the fourth direction $\delta$, and thus the insertion direction of the surgery cannula 210 is controlled by the rotary piezoelectric motor 260 and the linear piezoelectric motors 240. Specifically, an insertion depth of the surgery cannula 210 corresponds to the fifth direction $\zeta$, and thus the insertion depth of the surgery cannula 210 is controlled by the linear piezoelectric motors 250.

In some other embodiments of the present disclosure, the guiding element of the MRI-compatible stereotactic surgery device may include only one linear piezoelectric motor, instead of two linear piezoelectric motors. The only one linear piezoelectric motor of the guiding element of the MRI-compatible stereotactic surgery device of some other embodiments of the present disclosure is configured to drive the surgery cannula to move along the fourth direction. It is noted that, in some other embodiments of the present disclosure, the fifth direction is reserved for manual insertion of the surgery cannula by the surgeon. Furthermore, in some other embodiments of the present disclosure, there are scales labeled on the surgery cannula and/or there is a positioning component matching the surgery cannula, so as to control the amount of insertion.

It is noted that the MRI-compatible stereotactic surgery device 10 of the present disclosure only needs five degrees of freedom (DOF), i.e., the first direction $\theta_1$, the second direction $\theta_2$, the third direction $\theta_3$, the fourth direction $\delta$, and the fifth direction $\zeta$. In contrast, the traditional stereotactic surgery environments need six degrees of freedom or more than six degrees of freedom. Although more degrees of freedom represents larger stereotactic operating space, however, from a medical point of view, the stereotactic operating space of the brain neurosurgery for biopsy, ablation and/or deep brain stimulation (DBS) only need to cover the brain, and therefore the stereotactic surgery does not need too much work space. Therefore, the MRI-compatible stereotactic surgery device 10 having five degrees of freedom could reduce the requirement of the amount of the motors, thereby reducing the interference to the magnetic resonance (MR) image and reducing the volume of the entire device.

It is worth mentioning that the piezoelectric motor 131, the piezoelectric motor 151, the linear piezoelectric motor 240 and 250, and the rotary piezoelectric motor 260 are anti-magnetic piezoelectric motors which are made of non-magnetic piezoelectric ceramic material. The anti-magnetic piezoelectric motors are not driven by magnetic force, and therefore the anti-magnetic piezoelectric motors could be normally operated in environment with strong magnetic field. In addition, the anti-magnetic piezoelectric motors have a relatively high holding torque at rest, and thus when the MRI-compatible stereotactic surgery device 10 introduces external force to perform surgery cannula insertion, the motor shaft angle errors caused by the external force could be reduced.

It is worth mentioning that the MRI-compatible stereotactic surgery device 10 further includes plural electromagnetic interference shielding covers (not shown) respectively configured to cover the horizontal sliding stage 130, the vertical sliding stage 150, and the guiding element 200. The electromagnetic interference shielding covers are configured to electromagnetically shield the aforementioned anti-magnetic piezoelectric motors and the aforementioned optical encoders from interfering with the magnetic resonance (MR) image. The electromagnetic interference shielding covers could be copper shielding covers, but the present invention is not limited thereto. For example, aluminum or a material having low magnetic susceptibility or non-ferromagnetic material may be used as a material for forming the electromagnetic interference shielding covers.

It is worth mentioning that the MRI-compatible stereotactic surgery device 10 further includes plural fixed accessories (not shown) (e.g., screws, nuts, and so on) configured to fix plural mechanics parts of the base plate 110, the horizontal arc-shaped slide 120, the horizontal sliding stage 130, the vertical arc-shaped slide 140, the vertical sliding stage 150, the guiding element 200, the friction wheels 132 and 152, and the driven wheels 133 and 153. The fixed accessories could be made of copper, but the present invention is not limited thereto. For example, aluminum or a material having low magnetic susceptibility or non-ferromagnetic material may be used as a material for forming the fixed accessories with high tensile strength. Therefore, these fixed accessories having low magnetic susceptibility could avoid missile effect caused by the strong magnetic field, and reduce the eddy current generated by the RF pulse, and further reduce the heating effect and electromagnetic wave interference.

It is worth mentioning that the mechanics parts of the base plate 110, the horizontal arc-shaped slide 120, the horizontal sliding stage 130, the vertical arc-shaped slide 140, the vertical sliding stage 150, and the guiding element 200 are made of engineering plastics, such as polyoxymethylene (POM). The friction wheels 132 and 152, and the driven wheels 133 and 153 are made of synthetic rubber. The Young's modulus and the shear modulus of the engineering plastics are high enough and the magnetic susceptibility is low, and therefore the engineering plastics are suitable for the MRI-compatible stereotactic surgery device 10 because the engineering plastics could avoid electromagnetic wave interference and maintain the rigidity of the MRI-compatible stereotactic surgery device 10.

Figure 5:
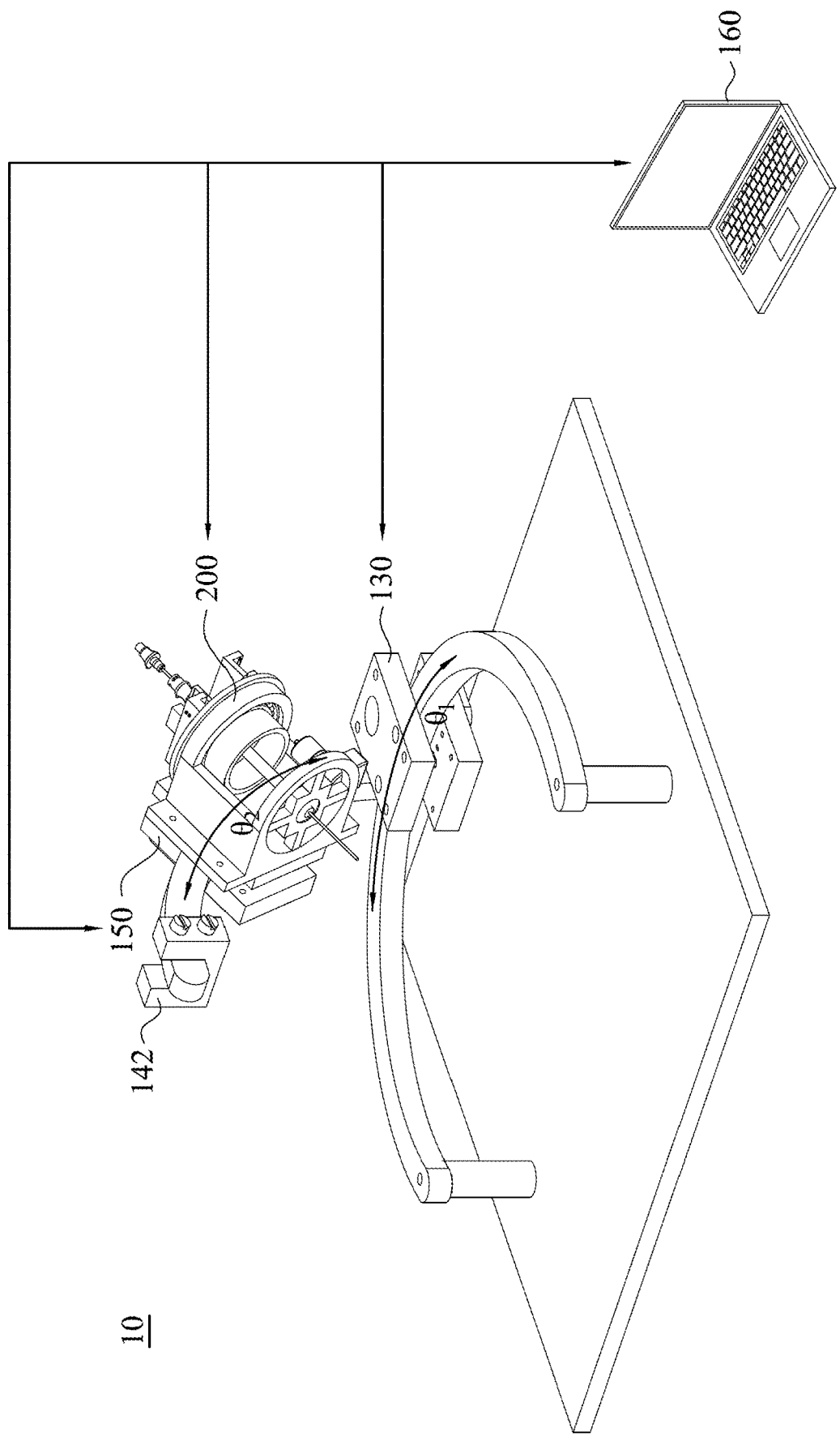
FIG. 5 illustrates the MRI-compatible stereotactic surgery device according to some embodiments of the present invention.

FIG. 5 illustrates the MRI-compatible stereotactic surgery device 10 according to some embodiments of the present invention. The MRI-compatible stereotactic surgery device 10 further includes a controlling computer 160 electrically connected to the piezoelectric motor 131 of the horizontal sliding stage 130, the piezoelectric motor 151 of the vertical sliding stage 150, the linear piezoelectric motors 240 and 250 and the rotary piezoelectric motor 260 of the guiding element 200. The controlling computer 160 is configured to drive the piezoelectric motors 131 and 151, the linear piezoelectric motors 240 and 250, and the rotary piezoelectric motor 260, thereby controlling the MRI-compatible stereotactic surgery device 10 with five degrees of freedom (i.e., the first direction $\theta_1$, the second direction $\theta_2$, the third direction $\theta_3$, the fourth direction $\delta$, and the fifth direction $\zeta$). The controlling computer 160 is further configured to reduce relative slide error between the friction wheel 132 and the horizontal arc-shaped slide 120 according to relative movement between the friction wheel 132 and the horizontal arc-shaped slide 120 which is recorded by the optical encoder 134; the controlling computer 160 is further configured to reduce relative slide error between the friction wheel 152 and the vertical arc-shaped slide 140 according to relative movement between the friction wheel 152 and the vertical arc-shaped slide 140 which is recorded by the optical encoder 154. It is worth mentioning that there are optical encoders respectively corresponding to the linear piezoelectric motors 240 and 250 and the rotary piezoelectric motor 260. Therefore, the controlling computer 160 could perform the closed-loop feedback control so as to reduce relative slide error according to the relative movement recorded by the optical encoder 134, the optical encoder 154, and the optical encoders respectively corresponding to the linear piezoelectric motors 240 and 250 and the rotary piezoelectric motor 260.

The MRI-compatible stereotactic surgery device 10 further includes plural signal lines (not shown) connected from the controlling computer 160 to the piezoelectric motors 131 and 151, the linear piezoelectric motors 240 and 250, and the rotary piezoelectric motor 260. It is noted that the aforementioned signal lines are covered by electromagnetic interference material (such as the tinned copper wire wrap) so as to avoid electromagnetic wave interference.

The controlling computer 160 is built in a forward kinematics model and an inverse kinematics model so as to calculate parameters corresponding to five degrees of freedom of the MRI-compatible stereotactic surgery device 10 and the perform a MRI-guided stereotactic surgery method, thereby driving the piezoelectric motors 131 and 151, the linear piezoelectric motors 240 and 250, and the rotary piezoelectric motor 260 to control the surgery cannula 210 to insert into suitable positon for the stereotactic surgery.

Figure 6:
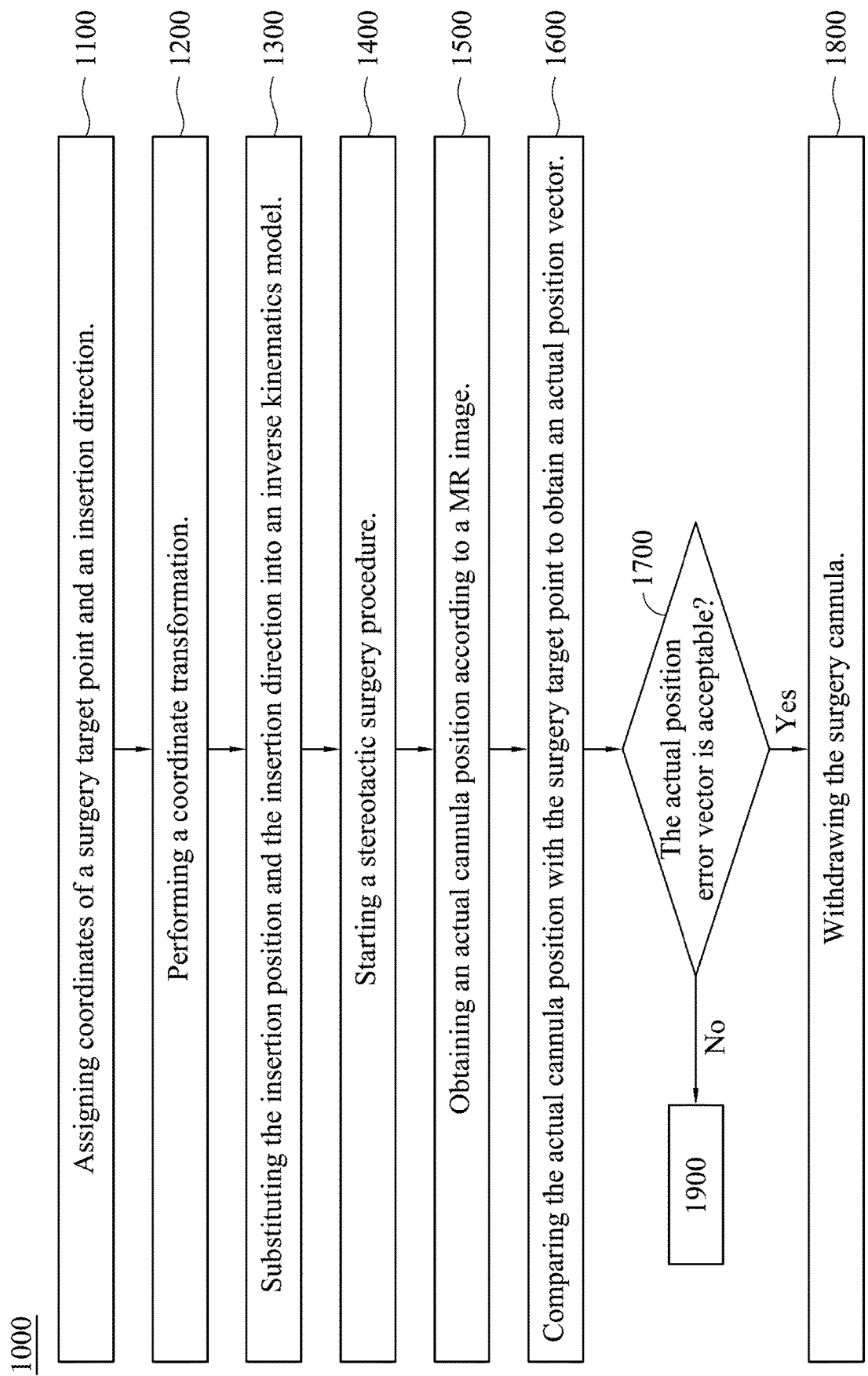
FIG. 6 illustrates the flow chart of the MRI-guided stereotactic surgery method according to some embodiments of the present invention.

FIG. 6 illustrates the flow chart of the MRI-guided stereotactic surgery method 1000 according to some embodiments of the present invention. The MRI-guided stereotactic surgery method 1000 includes the following steps 1100-1900. In step 1100, coordinates of a surgery target point of the surgery cannula 210 and an insertion direction of the surgery cannula 210 are assigned by, for example, the doctor. The coordinates of the surgery target point correspond to the coordinates in free space or the coordinates of a MRI scanner. In step 1200, a coordinate transformation is performed to transform the coordinates of the surgery target point into an insertion position of the surgery target point. It is noted that the insertion position and the insertion direction are suitable for the MRI-compatible stereotactic surgery device 10, and thus the controlling computer 160 of the MRI-compatible stereotactic surgery device 10 could therefore calculate parameters corresponding to five degrees of freedom of the MRI-compatible stereotactic surgery device 10, thereby controlling the surgery cannula 210 to perform the stereotactic surgery.

In step 1300, the insertion position and the insertion direction are substituted into the inverse kinematics model built in the controlling computer 160 to obtain five parameters respectively corresponding to five degrees of freedom of the MRI-compatible stereotactic surgery device 10. In some embodiments of the present disclosure, the parameters in step 1300 are obtained by utilizing a Newton-Raphson iterative method. Please note that the coordinate transformation in step 1200 and the computation of the inverse kinematics model in step 1300 are known in the related technical field, and thus the present disclosure will not further discuss.

In step 1400, the piezoelectric motors 131 and 151, the linear piezoelectric motors 240 and 250, and the rotary piezoelectric motor 260 of the MRI-compatible stereotactic surgery device 10 are controlled according to the parameters obtained in step 1300 so as to start a stereotactic surgery procedure, thereby inserting the surgery cannula 210 to perform the stereotactic surgery.

In step 1500, an actual cannula position is obtained according to a magnetic resonance (MR) image providing by a magnetic resonance imaging (MRI) scanner. It is noted that due to several kinds of the reasons, the actual cannula position of the surgery cannula 210 may not the same as the insertion position of the surgery cannula 210. Therefore, the MR image is required for fine tuning the inserting of the surgery cannula 210.

In step 1600, the actual cannula position is compared with the surgery target point to obtain an actual position vector. In some embodiments of the present disclosure, the actual position vector is obtained by subtracting the actual cannula position from the surgery target point.

After the step 1600, performing step 1700: determining whether the actual position vector is acceptable. When the actual position vector is acceptable, performing step 1800: withdrawing the surgery cannula to finish the stereotactic surgery procedure. When the actual position vector is not acceptable, performing step 1900.

Figure 7:
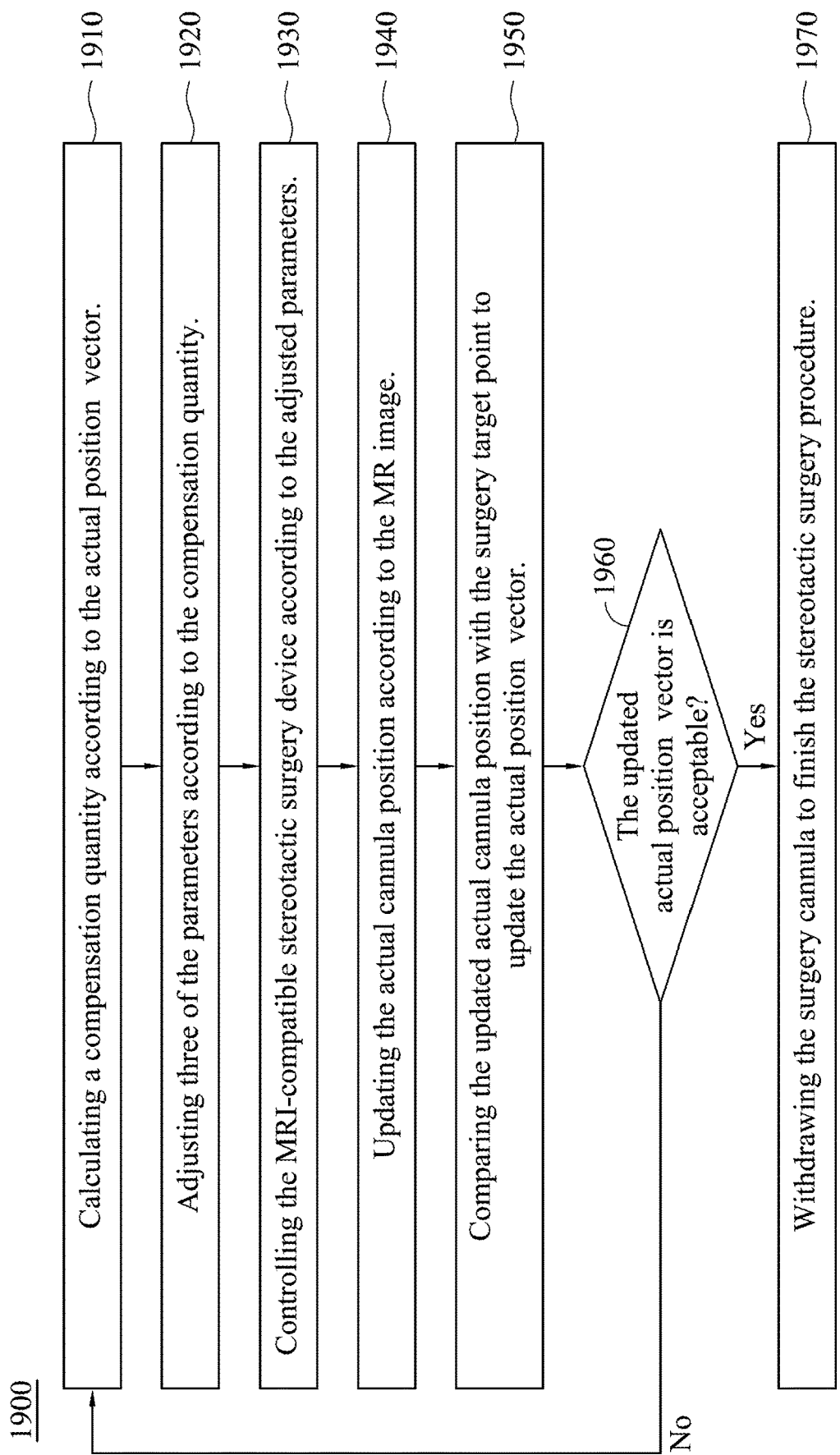
FIG. 7 illustrates the flow chart of one of steps of the MRI-guided stereotactic surgery method according to some embodiments of the present invention.

FIG. 7 illustrates the flow chart of the step 1900 of the MRI-guided stereotactic surgery method 1000 according to some embodiments of the present invention. The step 1900 includes steps 1910-1970. In step 1910, a compensation quantity is calculated according to the actual position vector obtained in step 1600. In some embodiment of the present disclosure, the compensation quantity $\Delta\theta$ is calculated by the following equations (1) and (2):

$$p(\theta^0 + \Delta\theta) \approx p(\theta^0) + \frac{\partial p}{\partial \theta}\bigg|_{\theta=\theta^0} \Delta\theta \quad (1)$$

$$p(\theta^0 + \Delta\theta) - p(\theta^0) = \frac{\partial p}{\partial \theta}\bigg|_{\theta=\theta^0} \Delta\theta$$

$$\Delta p = \frac{\partial p}{\partial \theta}\bigg|_{\theta=\theta^0} \Delta\theta$$

$$\Delta\theta = \left[\frac{\partial p}{\partial \theta}\bigg|_{\theta=\theta^0}\right]^{-1} \Delta p \quad (2)$$

$p=(p_x, p_y, p_z)$. $\theta=(\theta_3, \theta_4, \zeta)$. $\theta_4=\tan^{-1}(\delta/112.7)$. $\theta_0$ represents the parameters $\theta_3$, $\theta_4$, $\zeta$ corresponding to the actual cannula position. The above equation (1) represents that the compensation quantity $\Delta\theta$ is calculated by a Taylor series expansion around $\theta_0$. The above equations (1) and (2) represent that the compensation quantity $\Delta\theta$ is calculated by utilizing a Jacobian square matrix $$\left(\frac{\partial p}{\partial \theta}\right)$$

based on the actual position vector $\Delta p$, and the Jacobian square matrix $$\left(\frac{\partial p}{\partial \theta}\right)$$

are 3×3 square matrix so as to improve the compensating efficiency. The above equation (1) represents that the relationship between the compensation quantity $\Delta\theta$ and the actual position vector $\Delta p$. It is noted that the compensation (the compensation quantity $\Delta\theta$) and the corresponding adjustment are only directed at the third direction $\theta_3$, the fourth direction $\delta$, and the fifth direction $\zeta$ so as to fine tune the surgery cannula 210.

In step 1920, three of the parameters are adjusted according to the compensation quantity obtained in step 1910. In step 1930, the linear piezoelectric motors 240 and 250, and the rotary piezoelectric motor 260 of the MRI-compatible stereotactic surgery device 10 are controlled according to the adjusted parameters, thereby withdrawing the surgery cannula 210, adjusting the insertion position and the insertion direction of the surgery cannula 210, and inserting the surgery cannula 210 again. In step 1940, the actual cannula position is updated according to the MR image updating by the MRI scanner. In step 1950, the updated actual cannula position is compared with the surgery target point to update the actual position vector. After the step 1950, performing step 1960: determining whether the updated actual position vector is acceptable. When the updated actual position vector is acceptable, performing step 1970: withdrawing the surgery cannula to finish the stereotactic surgery procedure. When the updated actual position vector is not acceptable, performing back to step 1910.

It is noted that the traditional stereotactic surgery needs relatively long time for preoperative preparation and performing the operation. For example, the traditional stereotactic surgery needs to perform computed tomography (CT) and image registration between the MR image and CT image for preoperative preparation. The present disclosure does not need the computed tomography (CT) or the image registration between the MR image and CT image for preoperative preparation. For example, the traditional stereotactic surgery needs to perform the medical test (i.e., biopsy) to confirm the inserting position because the traditional stereotactic surgery does not have MR image to assist the inserting surgery. The present disclosure does not need to perform the biopsy medical test, the present disclosure utilizes the MR image for instantly feedback the cannula position. In other words, the MRI-guided stereotactic surgery method 1000 save more time for stereotactic surgery.

From the above description, the present disclosure provides the MRI-compatible stereotactic surgery device 10 and the MRI-guided stereotactic surgery method 1000. The MRI-compatible stereotactic surgery device 10 with five degrees of freedom is designed to be MRI-compatible, and therefore the MRI-compatible stereotactic surgery device 10 could be directly operated in the MRI environment. In other words, the MRI-compatible stereotactic surgery device 10 could avoid electromagnetic wave interference, thereby suitable for the MRI stereotactic surgery. The MRI-guided stereotactic surgery method 1000 utilizes the MR image to instantly guide the actual cannula position so as to correct inserting of the surgery cannula based on the instantly feedback MR image, thereby enhancing the accuracy and the efficiency of the stereotactic surgery and enhancing safety of the patients.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A MRI-compatible stereotactic surgery device, comprising:
   a remote center of motion (RCM) stage comprising:
      a base plate;
      a horizontal arc-shaped slide, wherein two ends of the horizontal arc-shaped slide are fixed on the base plate;
      a horizontal sliding stage disposed on the horizontal arc-shaped slide, wherein the horizontal sliding stage comprises a first friction wheel in rolling friction contact with the horizontal arc-shaped slide, wherein the horizontal sliding stage moves along the horizontal arc-shaped slide in a first direction through the first friction wheel, wherein the horizontal arc-shaped slide comprises a first driven wheel for recording relative movement between the first friction wheel and the horizontal arc-shaped slide;
      a vertical arc-shaped slide, wherein one end of the vertical arc-shaped slide is fixed on the horizontal sliding stage; and
      a vertical sliding stage disposed on the vertical arc-shaped slide, wherein the vertical sliding stage comprises a second friction wheel in rolling friction contact with the vertical arc-shaped slide, wherein the vertical sliding stage moves along the vertical arc-shaped slide in a second direction through the second friction wheel, wherein the vertical arc-shaped slide comprises a second driven wheel for recording relative movement between the second friction wheel and the vertical arc-shaped slide; and a guiding element fixed on the vertical sliding stage of the RCM stage, wherein the guiding element comprises a surgery cannula, wherein the guiding element is configured to guide the surgery cannula to move along a third direction, a fourth direction, and a fifth direction;

wherein the horizontal sliding stage further comprises a first optical encoder connected to the first driven wheel, wherein the first optical encoder is configured to measure amount of rotation of the first driven wheel, thereby recording relative movement between the first friction wheel and the horizontal arc-shaped slide;

wherein the vertical sliding stage further comprises a second optical encoder connected to the second driven wheel, wherein the second optical encoder is configured to measure amount of rotation of the second driven wheel, thereby recording relative movement between the second friction wheel and the vertical arc-shaped slide.

2. The MRI-compatible stereotactic surgery device of claim 1,
wherein the horizontal arc-shaped slide is ½ circular arc-shaped;
wherein the vertical arc-shaped slide is ¼ circular arc-shaped.

3. The MRI-compatible stereotactic surgery device of claim 1, further comprising:
at least one electromagnetic interference shielding cover configured to cover the horizontal sliding stage, the vertical sliding stage, and the guiding element; and
a plurality of fixed accessories configured to fix the base plate, the horizontal arc-shaped slide, the horizontal sliding stage, the vertical arc-shaped slide, the vertical sliding stage, the guiding element, the first friction wheel, the first driven wheel, the second friction wheel, and the second driven wheel, wherein the fixed accessories are made of non-ferromagnetic material;
wherein the base plate, the horizontal arc-shaped slide, the horizontal sliding stage, the vertical arc-shaped slide, the vertical sliding stage, and the guiding element are made of engineering plastics; wherein the first friction wheel, the first driven wheel, the second friction wheel, and the second driven wheel are made of synthetic rubber.

4. The MRI-compatible stereotactic surgery device of claim 1, wherein the guiding element further comprises:
two self-aligning universal ceramic bearings mounted on the surgery cannula so as to adjust an insertion direction of the surgery cannula.

5. The MRI-compatible stereotactic surgery device of claim 1,
wherein the horizontal sliding stage further comprises a first piezoelectric motor configured to drive the first friction wheel, such that the horizontal sliding stage moves along the horizontal arc-shaped slide in the first direction;
wherein the vertical sliding stage further comprises a second piezoelectric motor configured to drive the second friction wheel, such that the vertical sliding stage moves along the vertical arc-shaped slide in the second direction.

6. The MRI-compatible stereotactic surgery device of claim 1, wherein the guiding element further comprises:
a rotary piezoelectric motor configured to drive the surgery cannula to move along the third direction, wherein the rotary piezoelectric motor drives the surgery cannula through a synchronous timing belt and a belt pulley;
two linear piezoelectric motors respectively configured to drive the surgery cannula to move along the fourth direction and the fifth direction.

7. The MRI-compatible stereotactic surgery device of claim 1, wherein the guiding element further comprises:
a rotary piezoelectric motor configured to drive the surgery cannula to move along the third direction, wherein the rotary piezoelectric motor drives the surgery cannula through a synchronous timing belt and a belt pulley; and
a linear piezoelectric motor configured to drive the surgery cannula to move along the fourth direction;
wherein the fifth direction is reserved for manual insertion of the surgery cannula by a surgeon.

8. The MRI-compatible stereotactic surgery device of claim 6, further comprising:
a controlling computer connected to the first piezoelectric motor, the second piezoelectric motor, the linear piezoelectric motor, and the rotary piezoelectric motor, wherein the controlling computer is configured to drive the first piezoelectric motor, the second piezoelectric motor, the linear piezoelectric motor, and the rotary piezoelectric motor, thereby controlling the MRI-compatible stereotactic surgery device with five degrees of freedom.

9. The MRI-compatible stereotactic surgery device of claim 8,
wherein the controlling computer is further configured to reduce relative slide error between the first friction wheel and the horizontal arc-shaped slide according to relative movement between the first friction wheel and the horizontal arc-shaped slide which is recorded by the first optical encoder;
wherein the controlling computer is further configured to reduce relative slide error between the second friction wheel and the vertical arc-shaped slide according to relative movement between the second friction wheel and the vertical arc-shaped slide which is recorded by the second optical encoder.

10. The MRI-compatible stereotactic surgery device of claim 9, further comprising:
a plurality of signal lines connected from the controlling computer to the first piezoelectric motor, the second piezoelectric motor, the linear piezoelectric motors, and the rotary piezoelectric motor, wherein the signal lines are covered by electromagnetic interference material.

11. The MRI-compatible stereotactic surgery device of claim 9, wherein the controlling computer is built in a forward kinematics model and an inverse kinematics model.

12. The MRI-compatible stereotactic surgery device of claim 11, wherein the controlling computer is further configured to:
assign coordinates of a surgery target point of the surgery cannula and an insertion direction of the surgery cannula;
perform coordinate transformation to transform the coordinates of the surgery target point into an insertion position of the surgery target point;
substitute the insertion position and the insertion direction into the inverse kinematics model to obtain five parameters respectively corresponding to five degrees of freedom of the MRI-compatible stereotactic surgery device;

control the MRI-compatible stereotactic surgery device according to the parameters to start a stereotactic surgery procedure, thereby inserting the surgery cannula;

obtain an actual cannula position according to a MR image providing by a MRI scanner;

compare the actual cannula position with the surgery target point to obtain an actual position vector; and control the linear piezoelectric motors to withdraw the surgery cannula to finish the stereotactic surgery procedure when the actual position vector is acceptable.

13. The MRI-compatible stereotactic surgery device of claim 12, wherein when the actual position vector is not acceptable, the controlling computer is further configured to:

calculate a compensation quantity according to the actual position vector;

drive the linear piezoelectric motors and the rotary piezoelectric motor according to the compensation quantity, thereby withdrawing the surgery cannula, adjusting the insertion position and the insertion direction of the surgery cannula, and inserting the surgery cannula again;

update the actual cannula position according to the MR image updating by the MRI scanner;

compare the updated actual cannula position with the surgery target point to update the actual position vector; and withdraw the surgery cannula to finish the stereotactic surgery procedure when the updated actual position vector is acceptable.

14. The MRI-compatible stereotactic surgery device of claim 13, wherein the compensation quantity is calculated by a Taylor series expansion and by utilizing a Jacobian square matrix based on the actual position vector.

15. The MRI-compatible stereotactic surgery device of claim 13, wherein the parameters are obtained by utilizing a Newton-Raphson iterative method.

* * * * *